(12) United States Patent
Birnie et al.

(10) Patent No.: US 11,738,104 B2
(45) Date of Patent: Aug. 29, 2023

(54) STERTILIZING MEDIA CASSETTE

(71) Applicant: NCR Corporation, Atlanta, GA (US)

(72) Inventors: Steven Birnie, Dundee (GB); Liam McCafferty, Dundee (GB)

(73) Assignee: NCR Corporation, Atlanta, GA (US)

( * ) Notice: Subject to any disclaimer, the term of this patent is extended or adjusted under 35 U.S.C. 154(b) by 0 days.

(21) Appl. No.: 18/074,877

(22) Filed: Dec. 5, 2022

(65) Prior Publication Data

US 2023/0096257 A1 Mar. 30, 2023

Related U.S. Application Data

(62) Division of application No. 17/025,261, filed on Sep. 18, 2020, now Pat. No. 11,565,011.

(51) Int. Cl.
| | |
|---|---|
| *A61L 2/10* | (2006.01) |
| *G07D 11/13* | (2019.01) |
| *A61L 2/04* | (2006.01) |
| *A61L 2/26* | (2006.01) |
| *A61L 2/20* | (2006.01) |

(52) U.S. Cl.
CPC .................... *A61L 2/10* (2013.01); *A61L 2/04* (2013.01); *A61L 2/202* (2013.01); *A61L 2/26* (2013.01); *G07D 11/13* (2019.01); *A61L 2202/122* (2013.01); *A61L 2202/15* (2013.01); *A61L 2202/26* (2013.01)

(58) Field of Classification Search
CPC ... A61L 2/10; A61L 2/04; A61L 1/202; A61L 2/26; A61L 2202/122; A61L 2202/15; A61L 2202/26; G07D 11/13

USPC ............................ 250/453.11, 454.11, 455.11
See application file for complete search history.

(56) References Cited

U.S. PATENT DOCUMENTS

| | | | |
|---|---|---|---|
| 5,374,814 A | 12/1994 | Kako et al. | |
| 8,262,083 B2 | 9/2012 | Deas et al. | |
| 8,668,194 B2 | 3/2014 | Peters et al. | |
| 2002/0029728 A1 | 3/2002 | Walker | |

(Continued)

FOREIGN PATENT DOCUMENTS

| | | | | |
|---|---|---|---|---|
| CN | 203525028 | * | 9/2014 | ............... A45C 1/12 |
| CN | 209463433 | * | 10/2019 | ............... A45C 1/12 |

(Continued)

OTHER PUBLICATIONS

EP Search Report dated Oct. 1, 2021.

*Primary Examiner* — Nicole M Ippolito (74) *Attorney, Agent, or Firm* — NOTARO, MICHALOS & ZACCARIA P.C.; John S. Economou (57) ABSTRACT

A sterilizing media cassette is described for docking with a self-service terminal or a docking terminal. The sterilizing media cassette has a body having a lower portion and four sides. The body is adapted to hold a stack of media items such as banknotes on support members positioned above the lower portion of the body. A lid is provided that couples to the body. The lid forms an enclosed inner space when coupled to the body. An ozone gas source and/or a heat source is mounted on an inner surface of the body or the inner surface of the lid. A controller activates the ozone gas source and/or a heat source to sterilize the stack of media items. This may be done for a predetermined fixed period of time after the sterilizing media cassette is docked with a self-service terminal or a docking terminal.

9 Claims, 10 Drawing Sheets

(56) References Cited

U.S. PATENT DOCUMENTS

| | | |
|---|---|---|
| 2003/0071048 A1 | 4/2003 | Black et al. |
| 2007/0138263 A1 | 6/2007 | Tocher |
| 2012/0132654 A1 | 5/2012 | Leeper et al. |
| 2013/0026178 A1 | 1/2013 | Peters et al. |
| 2022/0008605 A1 | 1/2022 | Sood et al. |
| 2022/0072174 A1 | 3/2022 | Pragano |

FOREIGN PATENT DOCUMENTS

| | | |
|---|---|---|
| CN | 111341007 A | 6/2020 |
| KR | 101391303 B1 | 5/2014 |
| WO | 2019245490 A1 | 12/2019 |

\* cited by examiner

STERILIZING MEDIA CASSETTE

FIELD

This disclosure relates generally to a sterilizing media cassette, and more particularly to a media cassette such as an automatic teller machine (ATM) currency cassette adapted to sterilizing banknotes (paper money) stored therein.

BACKGROUND

Pathogens such as bacteria, protozoa, and viruses are infectious agents that can cause disease in humans and thus constitute a significant health hazard. A single banknote (e.g., a U.S. dollar bill) may be in circulation for over five years and may be handled by hundreds of people over the course of that time. The fibrous surface of most types of banknotes can harbor many types of pathogens, making each banknote in circulation a potential source of infection, depending on who has recently handled such banknote.

It can be difficult to disinfect a banknote. Common solutions used to disinfect hard surfaces, such as bleach, soap and water, isopropyl alcohol, hydrogen peroxide, etc., are not easily applied to banknotes and would likely damage the banknote in any event. Ultraviolet light is known to kill pathogens. However, to be most effective, the ultraviolet light should be applied to the surface harboring such pathogens for an extended period of time, e.g., thirty minutes. Ozone gas has been found effective in disinfecting banknotes, but ozone gas is harmful to humans and cannot simply be applied to banknotes in an ATM machine without a mechanism for recapturing the applied gas. Banknotes can be disinfected by the application of heat. In particular, the SARS coronavirus can be disinfected at a rate of 10000 units per 15 minutes when heated to a temperature of 56° C. ATMs are not currently adapted to apply heat in this manner to disinfect stored banknotes, however.

Media cassettes are used in self-service terminals such as automated teller machines (ATMs). ATMs use media cassettes for a variety of different types of media. However, the most common use of an ATM media cassette is for storing currency (in the form of banknotes) in a manner that allows the currency to be removed, one banknote at a time, from the media cassette (referred to as a currency cassette). The currency is typically stored as a horizontal stack within the currency cassette. To enable the stored banknotes to be removed reliably, the currency cassette includes a pusher plate that urges the horizontal stack towards a picking area. Currency cassettes are not presently adapted to disinfect or sterilize banknotes.

Accordingly, there is a need for a sterilizing media cassette that sterilizes banknotes stored in an ATM's currency cassette before being the banknotes are with withdrawn from the ATM to protect customers from possible exposure to any pathogens present on the banknotes.

BRIEF DESCRIPTION OF THE DRAWINGS

The following detailed description, given by way of example and not intended to limit the present disclosure solely thereto, will best be understood in conjunction with the accompanying drawings in which.

DETAILED DESCRIPTION

In the present disclosure, like reference numbers refer to like elements throughout the drawings, which illustrate various exemplary embodiments of the present disclosure.

Media cassettes are used in self-service terminals such as automated teller machines (ATMs). ATMs use media cassettes for a variety of different types of media. However, the most common use of an ATM media cassette is for storing currency (in the form of banknotes) or other media items in a manner that allows the currency to be removed, one banknote at a time, from the media cassette (also referred to as a currency cassette). The banknotes are typically stored as a horizontal stack within the media cassette. To enable the stored banknotes to be removed reliably, the media cassette includes a pusher plate that urges the horizontal stack towards a picking area.

Referring to FIGS. 1 to 4, a media cassette 10, in the form of a polycarbonate media cassette for storing banknotes or other media items, has a lid 12 which may be removable and secured to a body 14 by a latch 16 or any other suitable mechanism. Alternatively, lid 12 may be secured to body 14 by hinges and securely fastened to body 14 by the latch 16 or any other suitable fastening mechanism. The body 14 has a handle 18 pivotably mounted at a handle end 20, and a pick area 22 at a pick end 24 opposite the handle end 20.

A pusher plate 26 may be mounted on rails 40, 42 on each side of the cassette body, extending from the handle end 20 to the pick end 24, and is urged towards the pick end 24 by a resilient member (not shown). The pusher plate 26 is made of metal or other suitable material and is mounted above two lateral guides 30, 32 for providing a support surface for a lower level of banknotes 34 (shown in FIG. 4) and for guiding opposite short edges of banknotes 34 or other media as the banknotes are urged towards the pick end 24.

The body 14 has a roller shutter 36 covering the pick area 22, so that when the media cassette 10 is inserted into an ATM, other self-service terminal (SST), or recycler (not shown), metal fingers in the ATM engage with recesses (not shown) in the body 14, and the roller shutter 36 is automatically lowered by the metal fingers (or tines) to allow banknotes 34 to be picked from the pick area 22 by a media dispenser pick unit in the ATM. When the media cassette 10 is removed from the ATM, the tines in the ATM disengage from the recesses (not shown) in the body 14, and the roller shutter 36 is urged upwards to cover the pick area 22 and prevent access to the banknotes 34 in the media cassette 10.

The underside of the lid 12 includes two banknote long-edge aligners 38 mounted in slots in lid 12. The banknote long-edge aligners 38 prevent banknotes 34 stored within the media cassette 10 from moving towards the lid 12 during transportation.

Ultraviolet (UV) light cells are incorporated into media cassette 10 to sterilize the banknotes 34 (e.g., cash money) contained within media cassette 10. In particular, as shown in FIGS. 1 to 4, UV light cells are preferably mounted on each of the six inner surfaces of media cassette 10, with UV light sources 50, 52, 54, 56 placed on the side inner surfaces of body 14, UV light source 58 on the bottom inner surface of body 14, and UV light sources 60, 62, 64 on the inner surface of lid 12. Although three separate UV light sources 60, 62, 64 are shown on the inner surface of lid 12 but a single source extending the long length of the lid 12 would be adequate for the purposes of the present disclosure. In some applications, some of the UV light sources, e.g., the UV light sources 52, 56 at each end of body 14, may be omitted and suitable results may be obtained using a single UV light source mounted on an inner surface of body 14 or the lid 12. Sterilization through UV light will not harm the banknotes and, when applied in sufficient strength and for a sufficient duration, will kill any pathogens (e.g. SARS virus, Covid-19 virus, flu virus, etc.) present on the banknotes. Since UV light sterilization requires approximately thirty minutes to be effective, by incorporating the various UV light sources into the media cassette 10, the banknotes 34 contained within media cassette 10 can be sterilized during the cash-in-transit (or CIT) delivery process or after media cassette 10 is placed into the ATM cash dispenser mechanism. Since an ATM can take up to thirty minutes to start up, all the banknotes 34 in media cassette 10 can be sterilized during this time period. Sterilization can continue afterwards as well, for all banknotes 34 remaining in media cassette 10 as some of the banknotes 34 are withdrawn during normal use of the ATM. By sterilizing the banknotes 34 within a sealed media cassette 10, the sterilizing media cassette of the present disclosure ensures that there is no danger over-exposure UV light to either bank personnel or customers. The inner surface of media cassette 10 is preferably coated with a suitable protective UV coating to reflect the UV light within the sealed media cassette 10 and to prevent degradation of the media cassette 10 itself (which may be formed from an appropriate plastic material) due to UV light exposure.

Providing a sterilization mechanism within the media cassette 10 itself simplifies the effort required to implement banknote sterilization at the ATM, meaning that the time and cost required to implement banknote sterilization can be greatly reduced in contrast to other solutions. Media cassette 10 can also be used in conjunction with banknote recycling products (e.g., recyclers).

Figure 1:
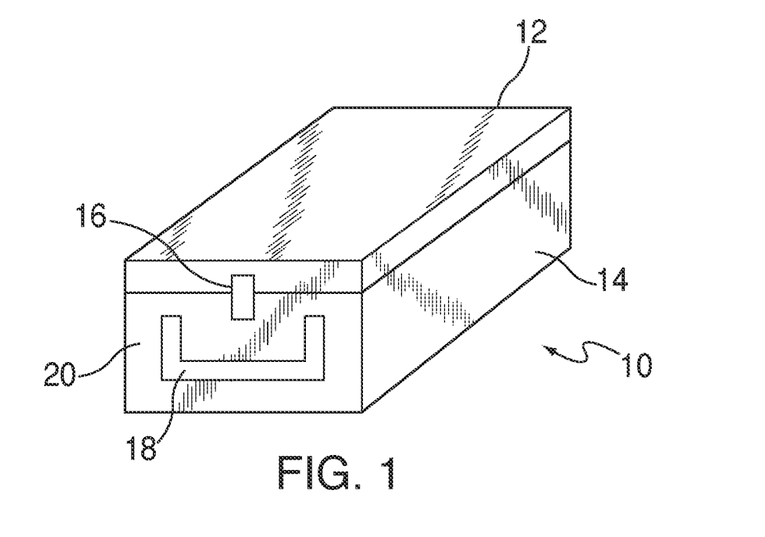
FIG. 1 is a schematic perspective view of a sterilizing media cassette according to an embodiment of the present disclosure.
Figure 2:
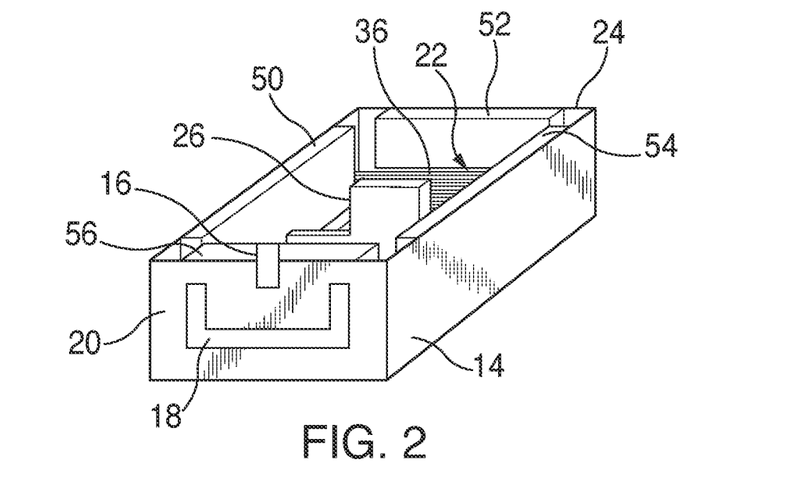
FIG. 2 is schematic perspective view of a body portion of the interior of the sterilizing media cassette of FIG. 1.
Figure 3:
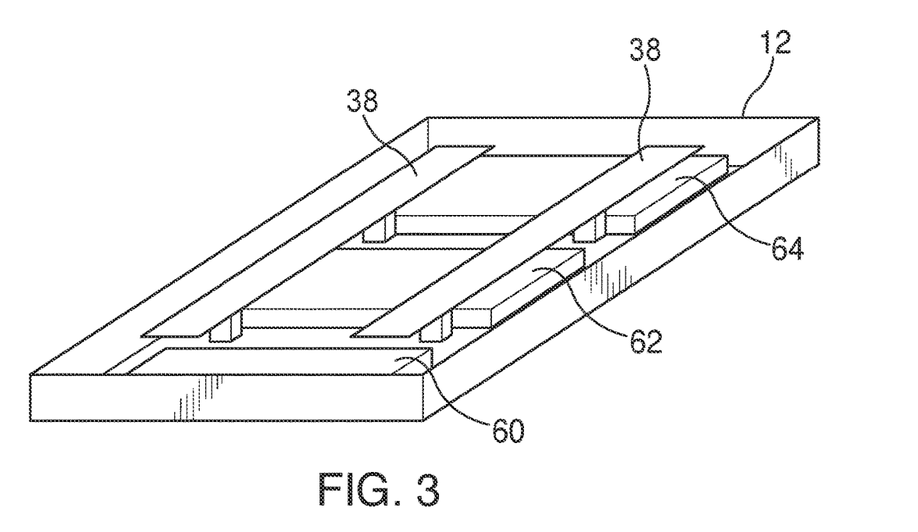
FIG. 3 is a schematic perspective underside view of a lid portion of the sterilizing media cassette of FIG. 1.
Figure 4:
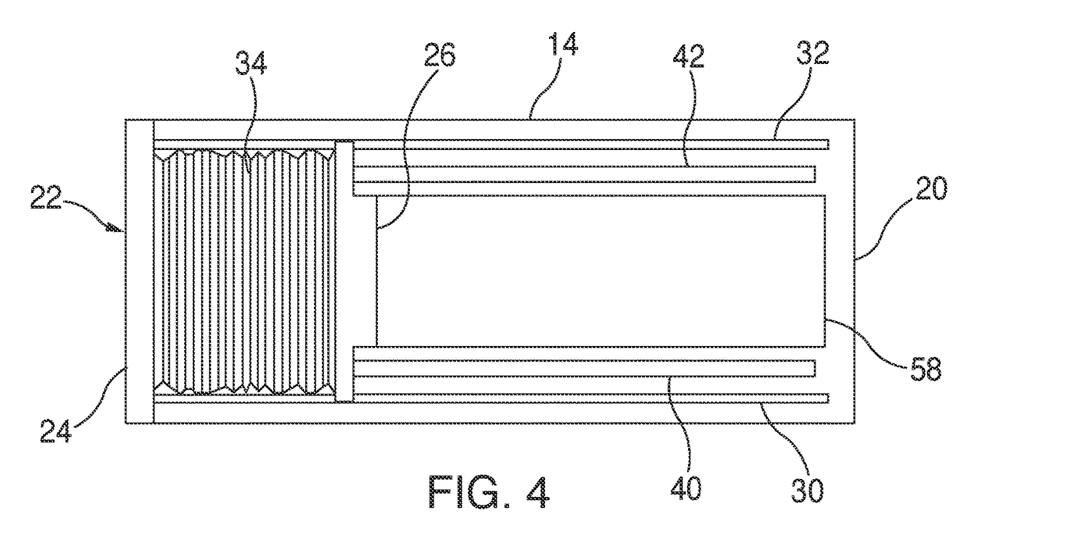
FIG. 4 is a schematic plan view of the body portion of the sterilizing media cassette of FIG. 1.
Figure 5:
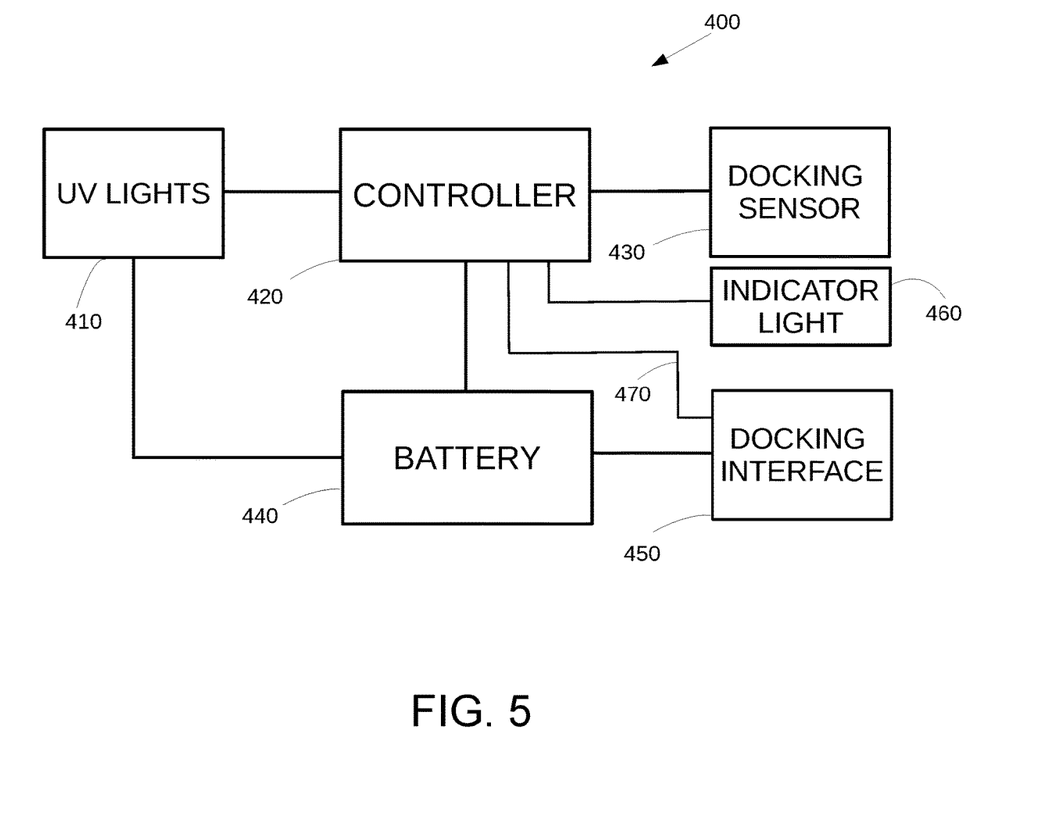
FIG. 5 is a block diagram of a banknote sterilizing system incorporated into the media cassette of FIG. 1.
Figure 15:
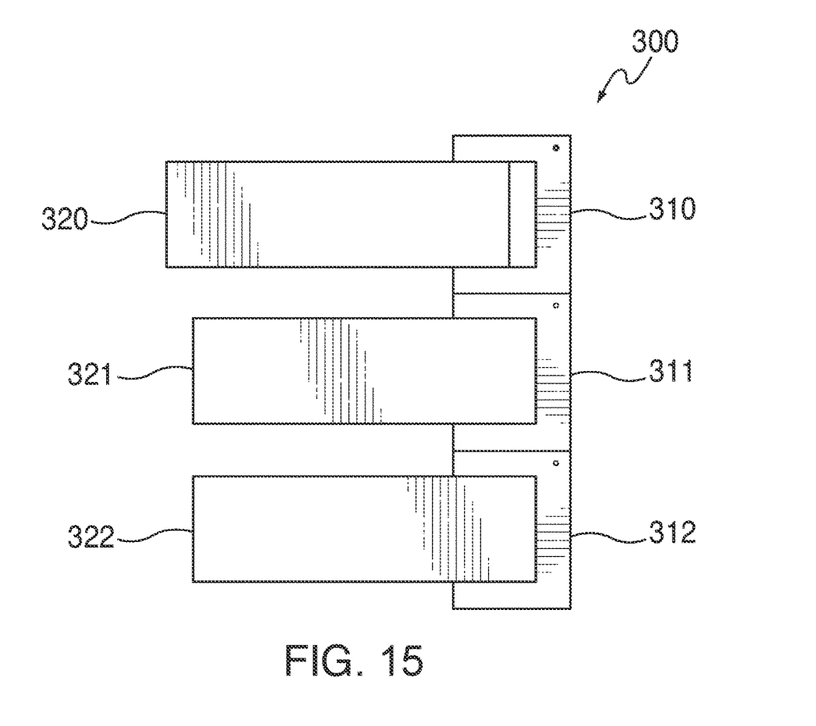
FIG. 15 is a diagram of a docking fixture for holding sterilizing media cassettes.

Referring now to FIG. 5, media cassette 10 includes one or more UV lights 410 (corresponding to one or more of UV light sources 50, 52, 54, 56, 58, 60, 62 shown in FIGS. 2 to 4) coupled to a controller 420 and to a power source such as battery 440. The controller 420 is also coupled to battery 440 for power and to a docking sensor 430 which provides a signal indicating that cassette has been docked, e.g., into a dispenser (ATM or other SST), a recycler, or an external dock located at a storage site or within a CIT van (as shown in FIG. 15). The battery 440 is coupled to a docking interface 450 that allows battery 440 to be recharged when docked. In some cases, battery 440 may omitted and power for controller 420 and the UV lights 410 is supplied directly via docking interface 450. Controller 420 activates UV lights 410 to start the sterilization process and to deactivate UV lights 410 at the completion of such process. For example, controller 420 may activate UV lights 410 when docking sensor 430 signals that media cassette 10 has been docked in order in order to sterilize the banknotes (or other media items) for a predetermined fixed period of time after docking. An indicator light 460 may be provided that is coupled to controller 420 to show status (i.e., that the sterilization process is ongoing) via an external portion of media cassette 10. Controller 420 may also provide a status signal line 470 via docking interface 450 used to signal the ATM, or other SST or recycler, that the sterilization process is ongoing and that the banknotes 34 within media cassette 10 should not be withdrawn. In the alternative, the ATM may be configured to wait for a fixed period of time, e.g., thirty minutes, after media cassette 10 is docked before withdrawing any banknotes from media cassette 10. The sterilization process can also be initiated during periods when the associated ATM is not in use, e.g., overnight.

Figure 6:
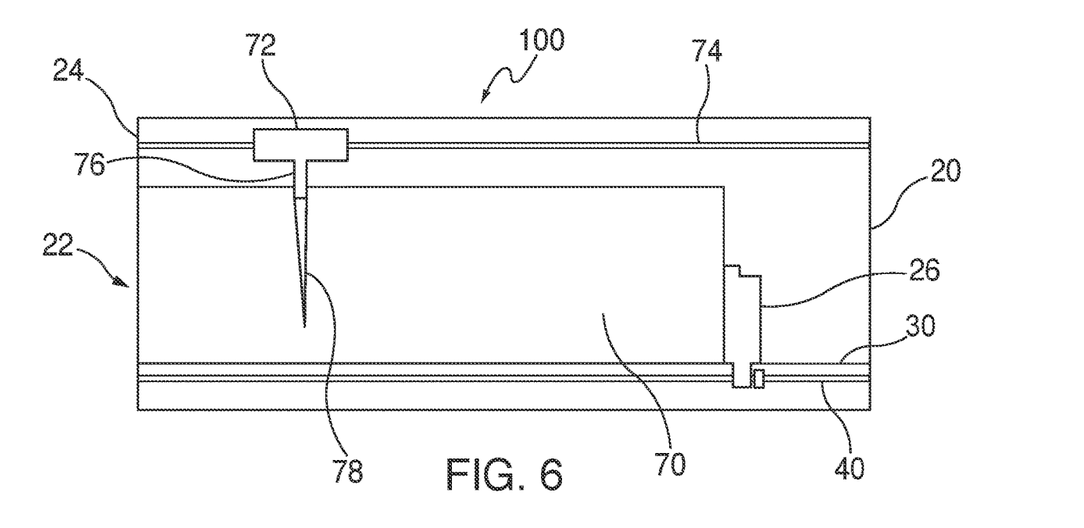
FIG. 6 is a simplified sectional side view of the body portion of an embodiment of the sterilizing media cassette of FIG. 1 illustrating a flicker mechanism for separating currency.

The UV light sterilization process is more effective when the UV light is provided to all surfaces of the banknotes within the sterilizing media cassette. Referring now to FIG. 6, a further embodiment of a sterilizing media cassette is shown in which a fanning mechanism 72 for fanning the banknotes 70 during the sterilization process is added to the media cassette 10 shown in FIGS. 1 to 4 and discussed above. In media cassette 100, the banknotes 70 are held on a lower surface formed by the lateral guides 30, 32 shown in FIG. 4 (only lateral guide 30 is shown in FIG. 6) via pusher plate 26 mounted on rails 42 and 40 (only rail 40 is shown in FIG. 6). The banknotes 70 are only supported on the lower surface at a small portion of each lower corner. An upper rail 74 is provided above the stack of banknotes 70. Fanning mechanism 72 is mounted to upper rail 74 and includes an arm 76 extending into the stacked banknotes 70. The moveable fanning mechanism 72 includes a motor (not shown) that moves fanning mechanism 72 back and forth along upper rail 74 between the pick end 24 of the stack of banknotes 70 and handle end 20 during the sterilization process (i.e., when the UV lights are activated). As the fanning mechanism 72 moves from one end to the other, arm 76 fans the stack of banknotes 70, creating a space 78 between adjacent banknotes with the stack of banknotes 70 and allowing UV light from the various UV light sources to penetrate into space 78 and sterilize exposed surfaces of each pair of exposed banknotes.

Figure 7:
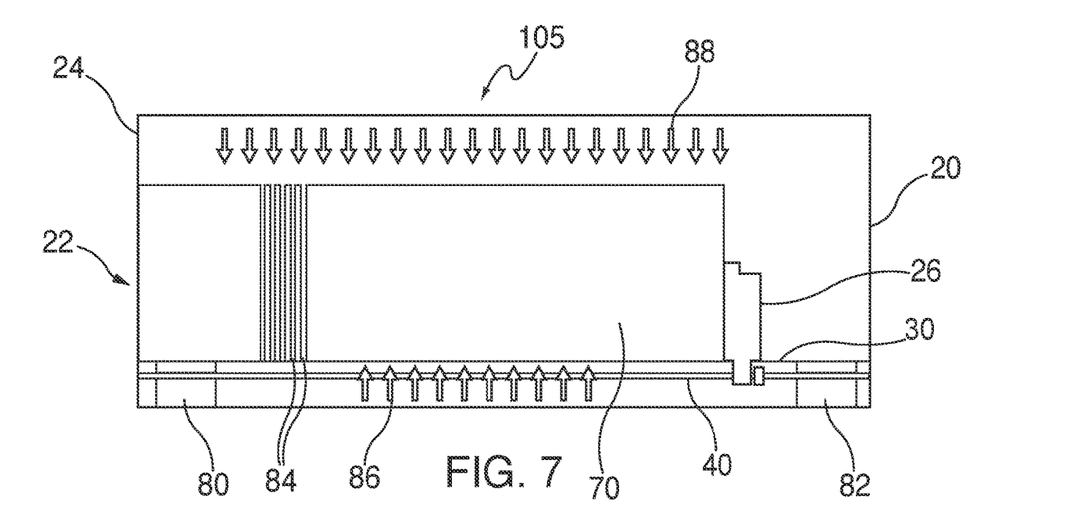
FIG. 7 is a simplified sectional side view of the body portion of an embodiment of the sterilizing media cassette of FIG. 1 illustrating a vibrating mechanism for separating currency.

Another further embodiment of sterilizing media cassette is shown in FIG. 7 which provides another method for separating adjacent banknotes within the stack of banknotes 70. This embodiment may be used in conjunction with or as an alternative to the embodiment of FIG. 5. In this embodiment, media cassette 105 includes two vibrating plates 80, 82 coupled to lateral guides 30, 32 that act as support members for the stack of banknotes 70. The vibrating plates 80, 82 are activated during the sterilization process and cause the banknotes 70 to move back and forth and thereby separate, generating spaces 84 that allow the UV light (represented by arrows 86, 88) to penetrate between the banknotes 70 to facilitate the sterilization process. Although two vibrating plates 80, 82 are shown, in some cases a single vibrating plate may be provided.

Figure 8:
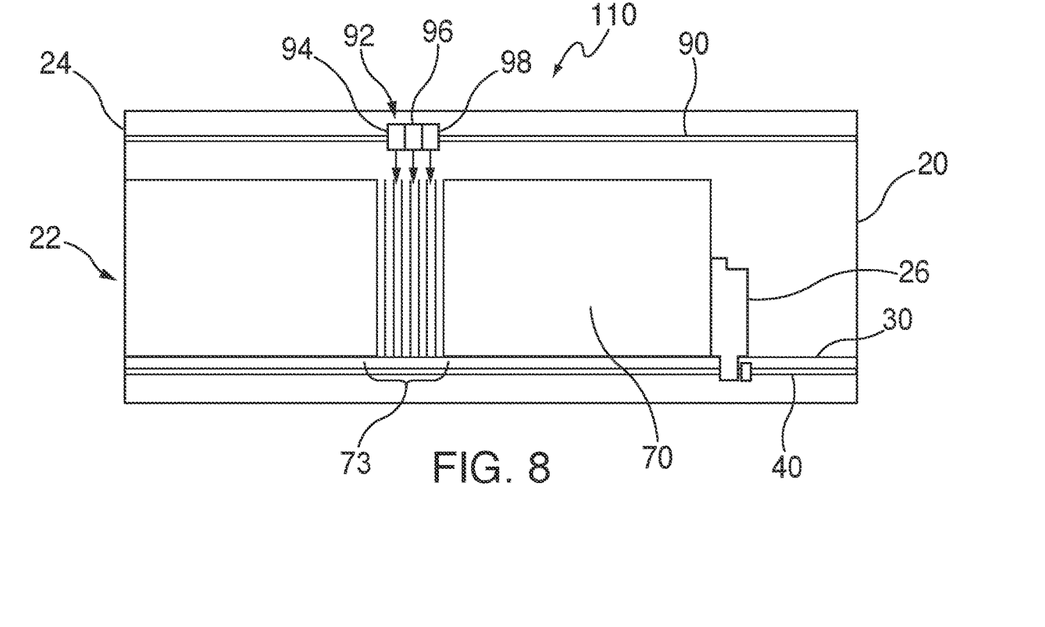
FIG. 8 is a simplified sectional side view of the body portion of an embodiment of the sterilizing media cassette of FIG. 1 illustrating an air injector mechanism for separating currency.

Yet another further embodiment of sterilizing media cassette is shown in FIG. 8 which provides another method for separating adjacent banknotes within the stack of banknotes 70. In this method, the media cassette 10 of FIGS. 1 to 4 is modified to include an air jet mechanism 92 mounted on an upper rail 90 above the stack of banknotes 70. The air jet mechanism 92 includes a motor (not shown) that moves the mechanism back and forth along upper rail 90 between the pick end 24 of the stack of banknotes 70 and handle end 20 during the sterilization process (i.e., when the UV lights are activated). The air jet mechanism 92 includes an air jet 96 that directs air downward, creating spacing between the stack of banknotes 70 as shown in the area 73. The air jet mechanism 92 may also include directed UV light sources 94, 98 for shining UV light directly into the spacing 73 created by air jet 96. UV light sources 94, 98 may be provided in addition to the UV light sources present in media cassette 10 or in place of such UV light sources. This embodiment also provides a cleaning action, removing any dirt or debris present on within the stack of banknotes 70 in response to the air flow provided by air jet 96.

Figure 9:
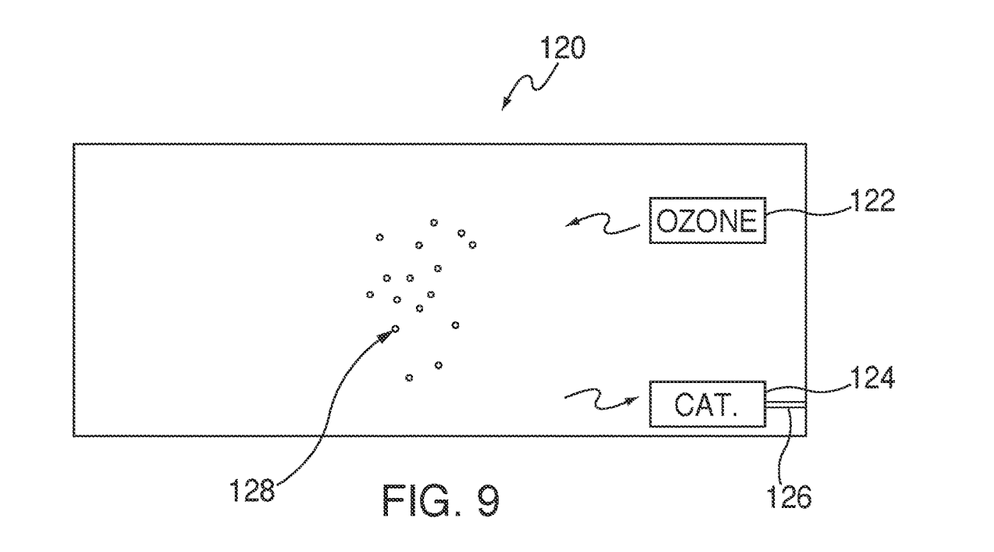
FIG. 9 is a block diagram of an ozone-based embodiment of a sterilizing media cassette.

Referring now to FIG. 9, a block diagram of an ozone-based sterilizing media cassette 120 is shown. An ozone cartridge 122 (or other type of ozone source) is provided within sterilizing media cassette 120 which, when docked to a dispenser (ATM or other SST), a recycler, or an external dock located at a storage site or within a CIT van (as shown in FIG. 15), releases ozone gas 128 into the interior of sterilizing media cassette 120 under the control of a controller (not shown) for a predetermined fixed period of time. Ozone is a powerful naturally-occurring oxidative agent that can destroy various pathogens such germs, viruses, and microbes that may cause surface or air contamination and leaves no chemical residue typical of alternative detergents or synthetic cleaners. Sterilizing media cassette 120 includes a lid that seals to the body (similar to lid 12 and body 14 as shown in FIGS. 1 to 4) when closed, in order to prevent any ozone gas from being released into the general atmosphere. In addition, sterilizing media cassette 120 includes a catalyst filter 124 which is used to evacuate the ozone gas from the interior of sterilizing media cassette 120 after the sterilization process, i.e., after completion of the predetermined fixed period of time. The catalyst filter 124 converts the ozone gas to oxygen so that it can be safely passed into the atmosphere outside of sterilizing media cassette 120 via a port 125 connected through an outer wall of the sterilizing media cassette 120 in order to pass the catalzyed ozone (oxygen) outside of the inner enclosure of sterilizing media cassette 120.

Figure 10:
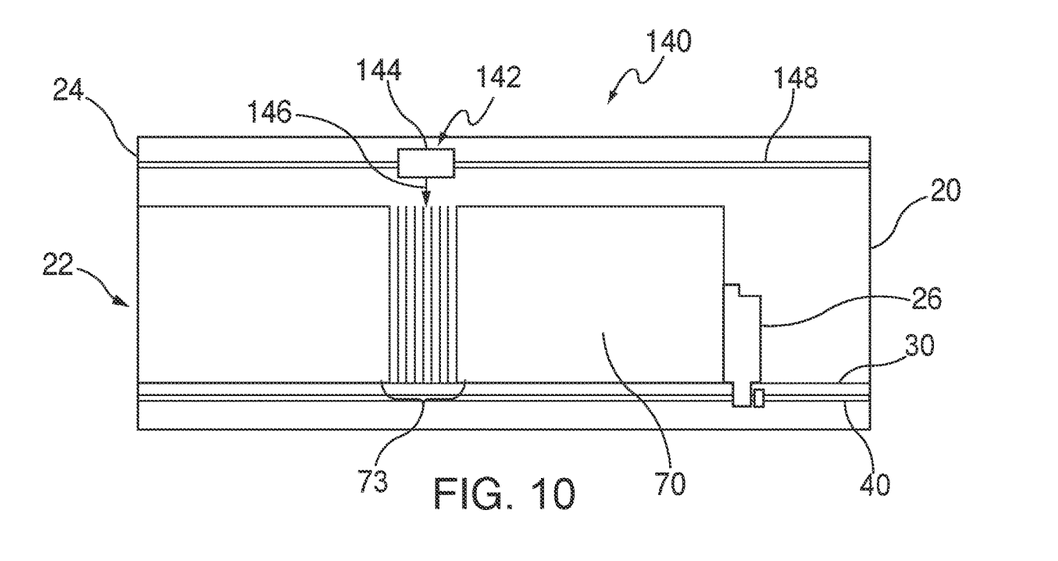
FIG. 10 is a simplified sectional side view of the body portion of an embodiment of the sterilizing media cassette of FIG. 1 illustrating an ozone injector mechanism for sterilizing currency.

A further embodiment of an ozone-based sterilizing media cassette 140 is shown in FIG. 10. Ozone-based sterilizing media cassette 140 includes an air jet mechanism 142 that is mounted on an upper rail 148 above the stack of banknotes 70. The air jet mechanism 142 includes a motor (not shown) that moves the mechanism back and forth along upper rail 148 between the pick end 24 of the stack of banknotes 70 and handle end 20 during the sterilization process (i.e., when the ozone gas has been released). The air jet mechanism 142 includes an air jet 144 that directs ozone downward as shown by arrow 146, creating spacing between the stack of banknotes 70 as shown in the area 73. The action of air jet 144 forces ozone into the spacing between banknotes 70 in the area 73, thereby improving the sterilization process by ensuring that the ozone gas penetrates between all of the banknotes with the stack of banknotes 70.

Figure 11:
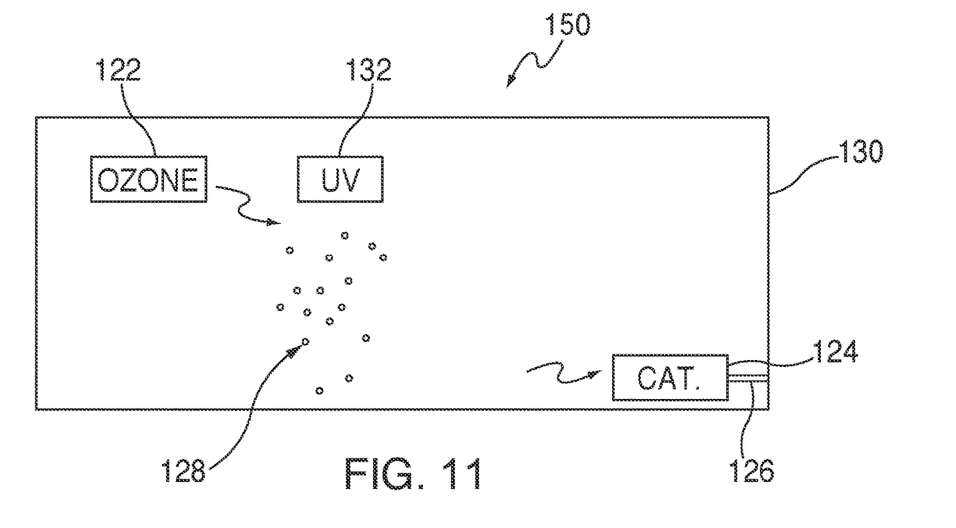
FIG. 11 is a block diagram of an embodiment of a sterilizing media cassette combining ultraviolet light and ozone.

A still further embodiment an ozone-based sterilizing media cassette 150 is shown in FIG. 11. Sterilizing media cassette 150 includes an ozone cartridge 122, catalyst filter 124, and port 126 which together operate in the same manner as the sterilizing media cassette 120 of FIG. 9 to flood the sealed interior chamber of sterilizing media cassette 150 with ozone gas 128 during the sterilization process. In addition, sterilizing media cassette 150 includes one or more UV light sources 132 which operate in the same manner as the various UV light sources shown in the embodiments of FIGS. 1 to 8. By combining the use of ozone gas and UV light during sterilization, the sterilization process can be quicker and more effective.

Figure 13:
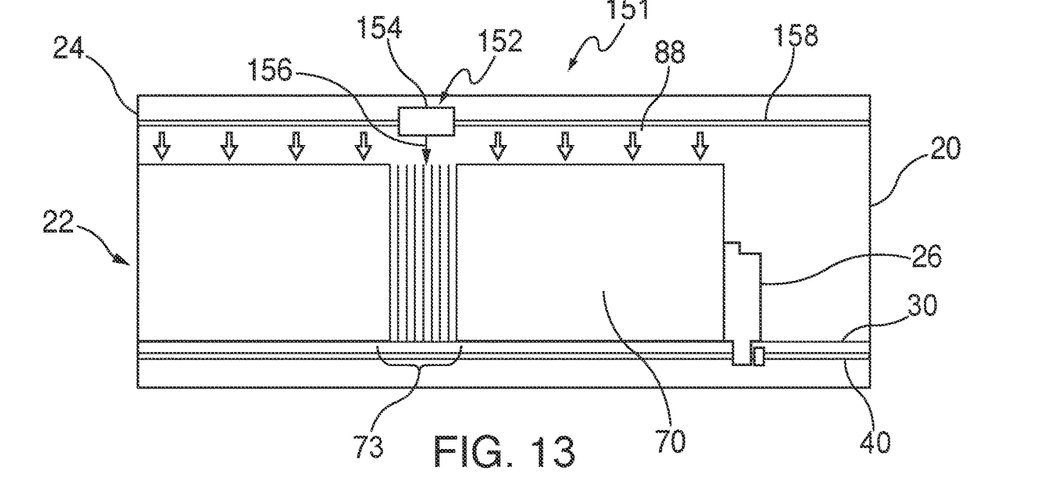
FIG. 13 is a simplified sectional side view of the body portion of an embodiment of the sterilizing media cassette of FIG. 1 illustrating a heated air injector mechanism for sterilizing currency.

A variation of the embodiment shown in FIG. 11 is shown in FIG. 13, where the ozone-based sterilizing media cassette 150 of FIG. 11 is modified as ozone-based sterilizing media cassette 151 to include both UV light sources as in the embodiment of FIGS. 1 to 4 and an air jet mechanism 152 that is mounted on an upper rail 158 above the stack of banknotes 70. The air jet mechanism 152 includes a motor (not shown) that moves the mechanism back and forth along upper rail 158 between the pick end 24 of the stack of banknotes 70 and handle end 20 during the sterilization process (i.e., when the ozone gas has been released). The air jet mechanism 152 includes an air jet 154 that directs air downward as shown by arrow 156, creating spacing between the stack of banknotes 70 as shown in the area 73. The action of air jet 154 forces ozone into the spacing between banknotes 70 in the area 73, thereby improving the sterilization process by ensuring that the ozone gas penetrates between all of the banknotes with the stack of banknotes 70. In addition, light from the UV light sources, represented by arrows 88, may also penetrate into the spacing between banknotes 70 in the area 73, thereby improving the sterilization process.

Referring now to FIGS. 12A to 12D, a number of embodiments of a sterilizing media cassettes are shown which provide a heated atmosphere within the sterilizing media cassette in order to more effectively sterilizing the banknotes present therein. For example, it is known that the SARS coronavirus can be disinfected at a rate of 10000 units per 15 minutes when heated to a temperature of 56° C.

Figure 12A:
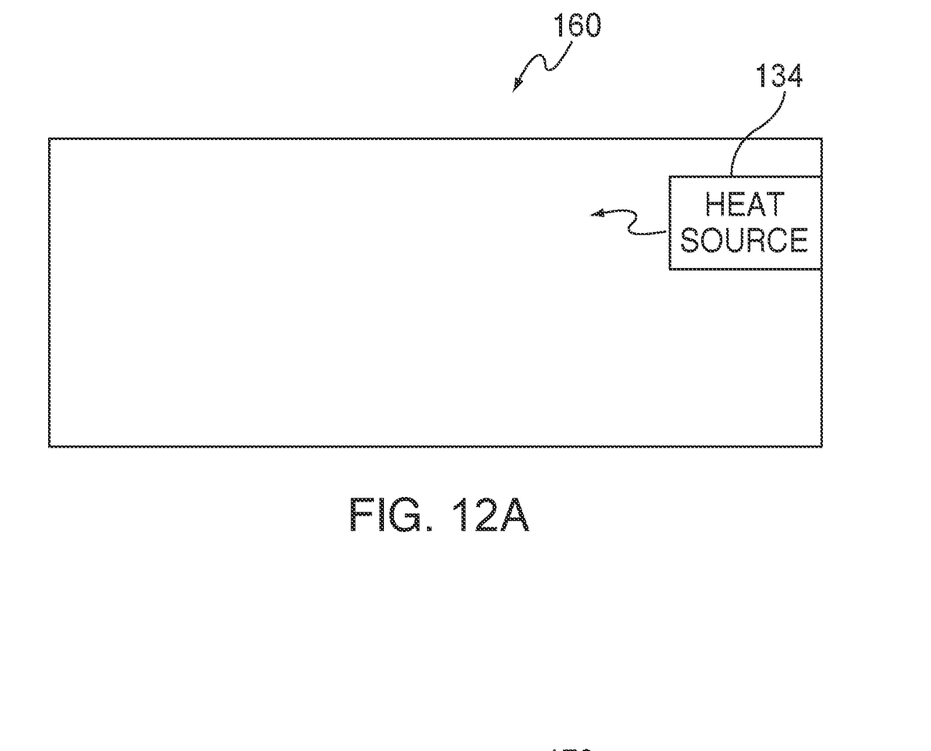
FIG. 12A is a block diagram of an embodiment of a sterilizing media cassette using heated hot air.

In the sterilizing media cassette 160 of FIG. 12A, a heat source 134 is provided which heats the interior portion of the sterilizing media cassette 160 during a heat-based sterilization process. This may be done, for example, for a fixed period of time. The heat source 134 may be a heater element included within sterilizing media cassette 160 or a heat exchanger which receives heat externally after docking with a self-service terminal or docking station.

Figure 12B:
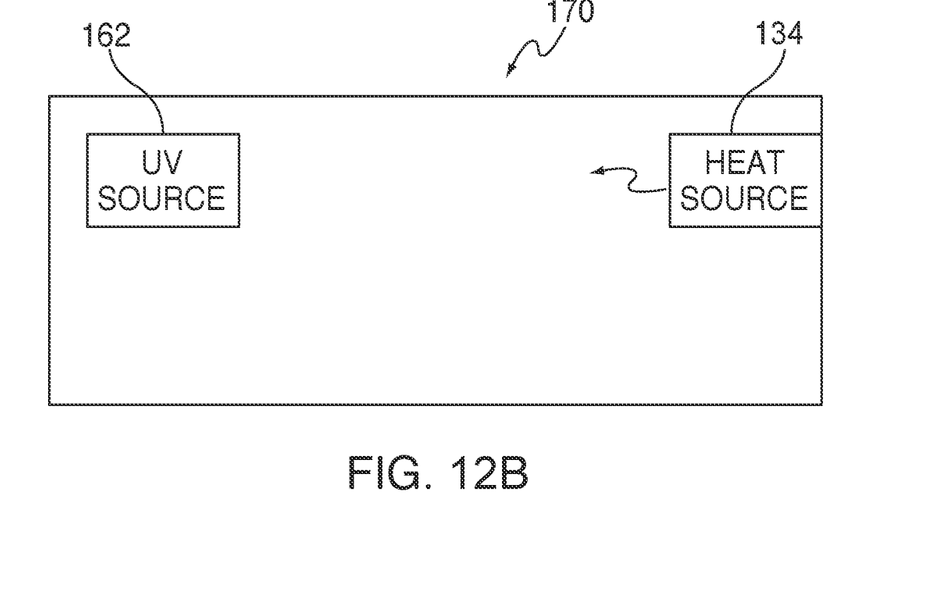
FIG. 12B is a block diagram of an embodiment of a sterilizing media cassette using heated hot air and ultraviolet light.

In one further embodiment shown in FIG. 12B, a sterilizing media cassette 170 includes both a heat source 134 and one or more UV light sources 162 which operate in the same manner as the various UV light sources shown in the embodiments of FIGS. 1 to 8. By combining the use of heat and UV light during sterilization, the sterilization process can be quicker and more effective than using only one type of sterilization method.

Figure 12C:
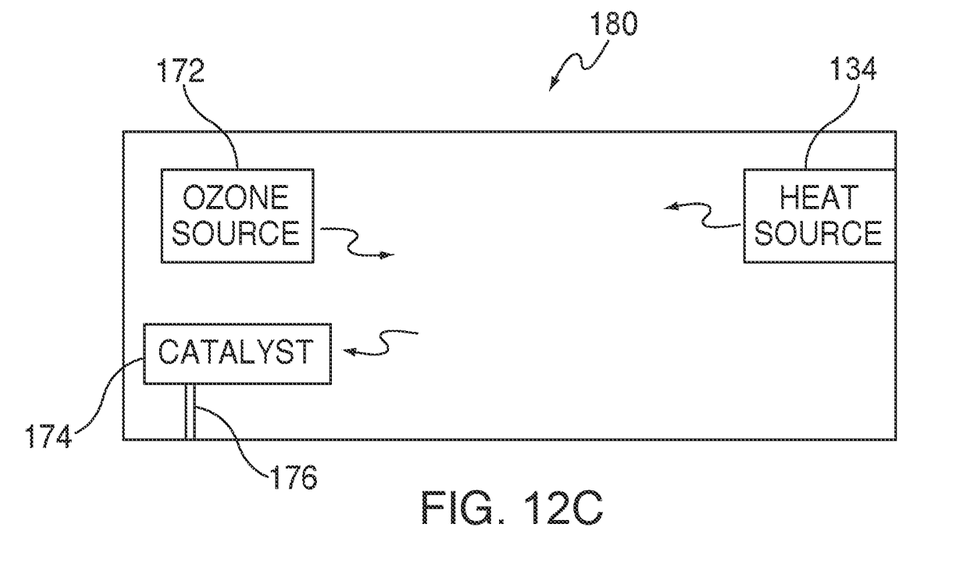
FIG. 12C is a block diagram of an embodiment of a sterilizing media cassette using heated hot air and ozone.

In another further embodiment shown in FIG. 12C, a sterilizing media cassette 180 includes both a heat source 134 and an ozone cartridge 122, catalyst filter 124, and port 126 which together operate in the same manner as the sterilizing media cassette 120 of FIG. 9 to flood the sealed interior chamber of sterilizing media cassette 180 with ozone gas 128 during the sterilization process. By combining the use of heat and ozone gas during sterilization, the sterilization process can also be quicker and more effective than using only one type of sterilization method.

Figure 12D:
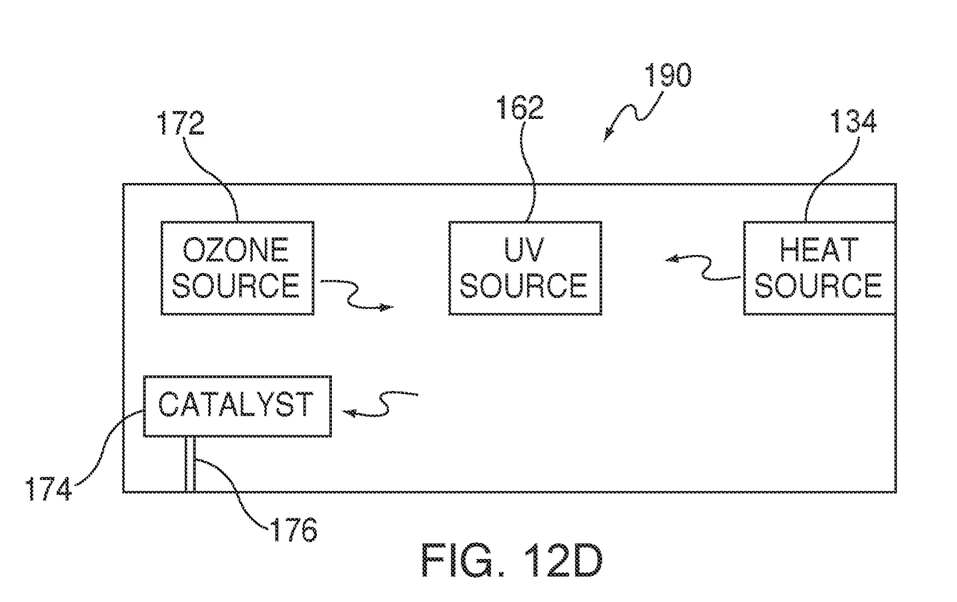
FIG. 12D is a block diagram of an embodiment of a sterilizing media cassette using heated hot air, ultraviolet light, and ozone.

In a still further embodiment shown in FIG. 12D, a sterilizing media cassette 190 includes a heat source 134, one or more UV light sources 162 which operate in the same manner as the various UV light sources shown in the embodiments of FIGS. 1 to 8, and an ozone cartridge 122, catalyst filter 124, and port 126 which together operate in the same manner as the sterilizing media cassette 120 of FIG. 9 to flood the sealed interior chamber of sterilizing media cassette 180 with ozone gas 128 during the sterilization process. By combining the use of heat, UV light, and ozone gas during sterilization, the sterilization process can also be quicker and more effective than using only one type of sterilization method.

Figure 14A:
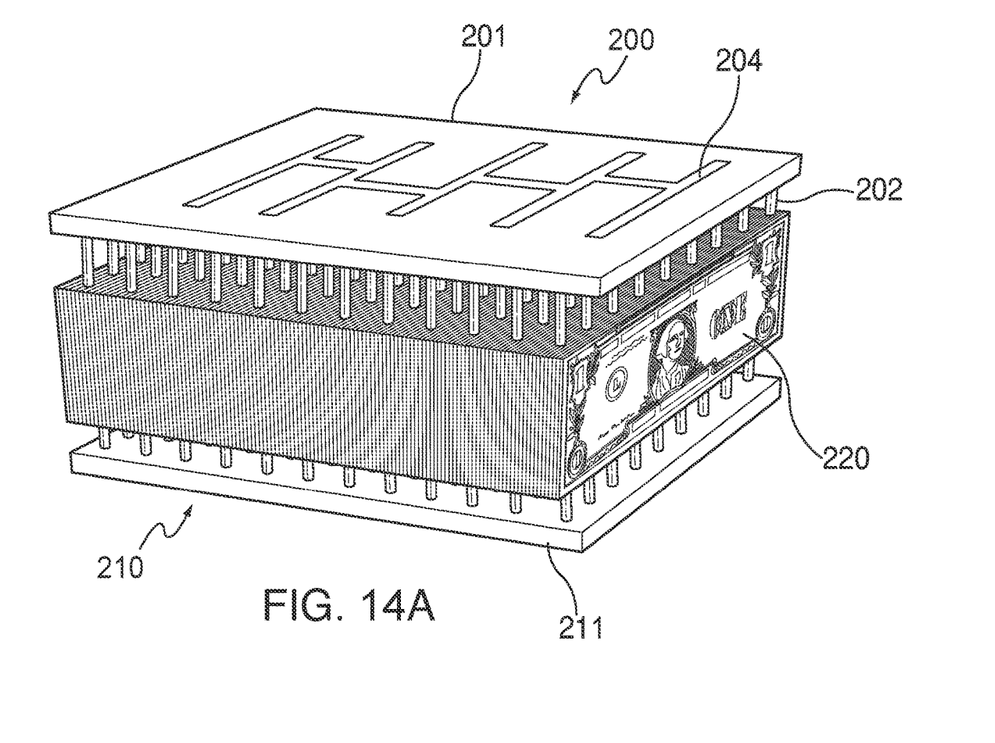
FIGS. 14A and 14B are diagrams of a fixture for applying ultraviolet light to currency via light pipes.
Figure 14B:
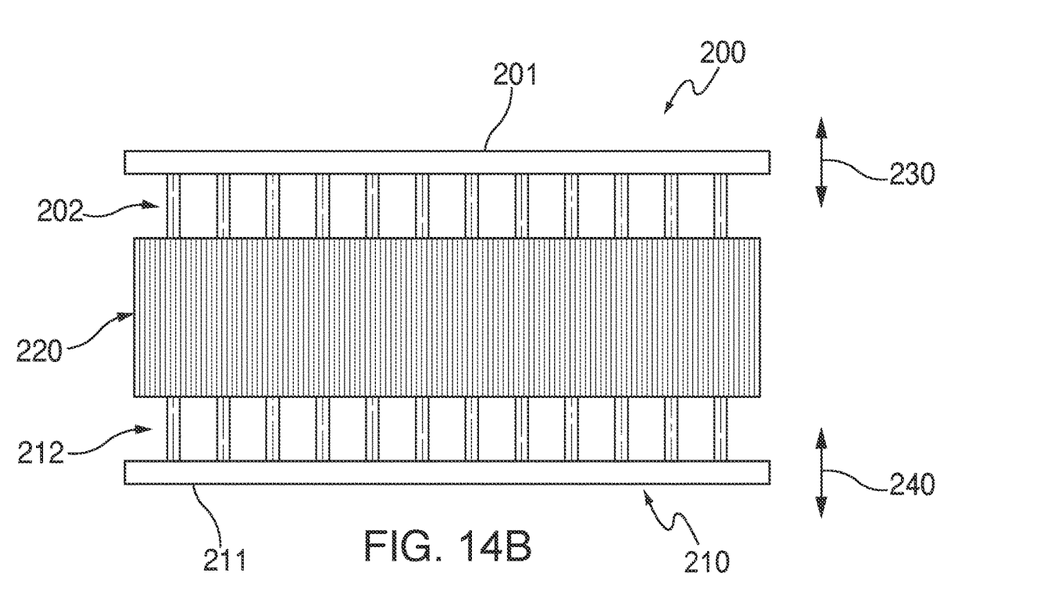

Referring now to FIGS. 14A and 14B, specialized fixtures 200, 210 may be provided for inserting UV light between banknotes within the stack of banknotes 220 included within a sterilizing media cassette of the present disclosure. Each fixture 200, 210 consists of a base plate 201, 211 having a series of UV light sources mounted in a channel therein (e.g., see channel 204 in FIG. 14A) the UV light sources are optically coupled to semi-rigid plastic light pipes 202, 212 that extend downward (for fixture 200) or upward (for fixture 210) and coupled to a power source and controller for activation in a manner similar to that shown in FIG. 5. The fixtures 200, 210 may be mounted in a manner in which each fixture 200, 210 is in a fixed position within the sterilizing media cassette adjacent to an outer surface of the stack of banknotes 220 so that each of the light pipes 202, 212 extend into the stack of banknotes 220. This allows UV light to be directed between each banknotes that is adjacent to each of the light pipes 202, 212. By making each light pipe semi-rigid, the UV lights can be activated at all times after the sterilizing media cassette is docked, and because each light pipe is only semi-rigid, the banknotes in the stack of banknotes 220 may be moved laterally as required during normal use, thereby ensuring that all of the bills will likely be exposed to UV light from the light pipes 202, 212 before being withdrawn, etc. In the alternative, each fixture 200, 210 may be coupled to a motorized mechanism which moves the fixtures up and down in the direction shown by arrows 230, 240 during the sterilization process or during normal use. For example, each fixture 200, 210 may be inserted against the stack of banknotes 220 and activated whenever the associated ATM is not being used, and withdrawn during use only.

As shown in FIG. 15, a docking station 300 may be provided for a storage site or a CIT van for activating the sterilization process while in storage or transit. Docking station 300 includes a plurality of docking bays 310, 311, 312 for mating with media cassettes 320, 321, 322 via a docking interface (not shown). The docking interface provides power for either directly powering each media cassette or for charging a battery included within each media cassette. Although three bays 310, 311, 312 are shown, this number is merely an example and the number of bays used depends on the particular installation.

The various embodiments of a sterilizing media cassette are contained within the volume of a conventional media cassette, making these embodiments an optional feature available to customers for upgrade. This also limits the amount of development required on any cash dispenser (ATM) or recycler to enable use with the sterilizing media cassette of the present disclosure.

Although the present disclosure has been particularly shown and described with reference to the preferred embodiments and various aspects thereof, it will be appreciated by those of ordinary skill in the art that various changes and modifications may be made without departing from the spirit and scope of the disclosure. It is intended that the appended claims be interpreted as including the embodiments described herein, the alternatives mentioned above, and all equivalents thereto.

What is claimed is:

1. A sterilizing media cassette, comprising:
   a body having a lower portion and four sides, the body adapted to hold a stack of media items in a position above the lower portion of the body;
   a lid that couples to the body, the lid forming an enclosed inner space within the sterilizing media cassette when the lid is coupled to the body;
   an ozone gas source mounted on an inner surface of the body or the lid that is activated for a predetermined fixed period of time to provide ozone gas to sterilize the stack of media items; and
   a catalyst filter that converts the ozone gas to oxygen after completion of the predetermined fixed period of time.

2. The sterilizing media cassette of claim 1, further comprising a port coupled to the catalyst filter and to atmosphere outside the enclosed inner space within the sterilizing media cassette in order to pass the oxygen produced by the catalyst filter out of the enclosed inner space.

3. The sterilizing media cassette of claim 1, further comprising an air jet mechanism mounted adjacent to a surface of the stack of media items, the air jet mechanism moving back and forth between a first end of the stack of media items and a second end of the stack of media items during the predetermined fixed period of time to direct ozone into spaces between adjacent media items by an air jet incorporated into the air jet mechanism as the air jet mechanism moves between the first end of the stack of media items and the second end of the stack of media items.

4. The sterilizing media cassette of claim 3, further comprising UV light sources incorporated into the air jet mechanism adjacent to the air jet which are activated during the predetermined fixed period of time to direct UV light into spaces formed by the air jet.

5. The sterilizing media cassette of claim 1, further comprising a UV light fixture comprising a base, a plurality of UV light sources mounted in the base, and a plurality of semi-rigid light pipes which extend outward from a surface of the base and optically coupled to the UV light sources, the UV light fixture adapted to be inserted against the stack of media items from an outer surface thereof so that each of the plurality of semi-rigid light pipes extend between adjacent media items among the stack of media items, the UV light sources activated for the predetermined fixed period of time to sterilize the stack of media items.

6. The sterilizing media cassette of claim 1, further comprising a heat source mounted on an inner surface of the body or the lid that is activated for the predetermined fixed period of time to sterilize the stack of media items.

7. A sterilizing media cassette, comprising:
a body having a lower portion and four sides, the body adapted to hold a stack of media items in a position above the lower portion of the body;
a lid that couples to the body, the lid forming an enclosed inner space when coupled to the body;
a heat source mounted on an inner surface of the body or the lid that is activated to sterilize the stack of media items; and
a UV light fixture comprising a base, a plurality of UV light sources mounted in the base, and a plurality of semi-rigid light pipes which extend outward from a surface of the base and optically coupled to the UV light sources, the UV light fixture adapted to be inserted against the stack of media items from an outer surface thereof so that each of the plurality of semi-rigid light pipes extend between adjacent media items among the stack of media items, the UV light sources activated to sterilize the stack of media items.

8. A sterilizing media cassette, comprising:
a body having a lower portion and four sides, the body adapted to hold a stack of media items in a position above the lower portion of the body;
a lid that couples to the body, the lid forming an enclosed inner space when coupled to the body; and
a heat source mounted on an inner surface of the body or the lid that is activated to sterilize the stack of media items;
wherein the heat source is activated for a predetermined fixed period of time to sterilize the stack of media items.

9. A sterilizing media cassette, comprising:
a body having a lower portion and four sides, the body adapted to hold a stack of media items in a position above the lower portion of the body;
a lid that couples to the body, the lid forming an enclosed inner space within the sterilizing media cassette when the lid is coupled to the body;
an ozone gas source mounted on an inner surface of the body or the lid that is activated for a predetermined fixed period of time to provide ozone gas to sterilize the stack of media items; and
a heat source mounted on the inner surface of the body or the lid that is activated to sterilize the stack of media items.

\* \* \* \* \*